United States Patent [19]  [11] 4,021,460
Ogoshi et al.  [45] May 3, 1977

[54] METHOD FOR MANUFACTURING α-SULFO FATTY ACID ESTER SALT

[75] Inventors: Toshiaki Ogoshi, Funabashi; Shizuo Sekiguchi, Yokohama, both of Japan

[73] Assignee: Lion Fat & Oil Co., Ltd., Tokyo, Japan

[22] Filed: Oct. 7, 1975

[21] Appl. No.: 620,278

[30] Foreign Application Priority Data

Oct. 8, 1974  Japan ............................ 49-115813

[52] U.S. Cl. ............................... 260/400; 260/401
[51] Int. Cl.² ............................................ C11D 1/28
[58] Field of Search ............................ 260/400, 401

[56] References Cited

UNITED STATES PATENTS

| | | | |
|---|---|---|---|
| 3,089,882 | 5/1963 | Schenck et al. | 260/400 |
| 3,162,657 | 12/1964 | Gordon et al. | 260/400 |
| 3,558,676 | 1/1971 | Doherty | 260/400 |

Primary Examiner—Patrick P. Garvin
Attorney, Agent, or Firm—Carroll F. Palmer

[57] ABSTRACT

A method for manufacturing α-sulfo fatty acid ester salt which comprises the steps of sulfonating a mixture of 100 parts by weight of saturated fatty acid alkyl ester having 9 to 26 carbon atoms and less than 10 parts by weight of inorganic sulfate by sulfonating gas containing 1.0 to 2.0 mols of $SO_3$ per mol of said fatty acid ester and diluted to a concentration of 3 to 20% by volume by inert gas at a higher reaction temperature than the solidification point of said fatty acid ester, followed by neutralization by caustic alkali. According to this method, an amount of by-product yielded by breakage of an ester linkage is decreased with the resultant lowered coloration of the product. α-sulfo fatty acid ester salt is used preferably as an active component for a detergent composition.

7 Claims, No Drawings

METHOD FOR MANUFACTURING α-SULFO FATTY ACID ESTER SALT

BACKGROUND OF THE INVENTION

This invention relates to a method for manufacturing α-sulfo fatty acid ester salt employed as an active component for a detergent composition. α-sulfo fatty acid ester salt is produced by sulfonating fatty acid ester with $SO_3$ and followed by neutralization by alkali. As the sulfonation of fatty acid ester proceeds at a slow speed, it is necessary that the sulfonated product be digested. The coloration of the product is pronounced due to fair excess of $SO_3$ and it is therefore necessary that it be subjected to severe bleaching process. Even in this case, it is difficult to obtain a satisfactory color tone. Breakage of ester linkage occurs during the sulfonation, neutralization or bleaching of fatty acid ester. A by-product, for example, α-sulfo fatty acid di-soda salt yielded by breakage of ester linkage is poor in detergency, when used as an active component for a detergent composition. It is, therefore, desired that the yield or remaining percentage of 60 -sulfo fatty acid ester salt be elevated by suppressing the growth of any by-product as much as possible.

A 2-stage sulfonation method, a sulfonated product-esterifying method etc. are proposed for improvement of the fatty acid ester-sulfonating method, but no satisfactory result is obtained owing to the performance of the product as well as the complexity of the process.

SUMMARY OF THE INVENTION

An object of this invention is to provide a method for increasing the yield of α-sulfo fatty acid ester salt in its production by sulfonation of fatty acid ester.

Another object of this invention is to provide a method for manufacturing α-sulfo fatty acid ester salt lower in coloration.

This invention is based on the discovery that, in a method for manufacturing α-sulfo fatty acid ester salt by sulfonating fatty acid by $SO_3$, followed by neutralization by alkali, when inorganic sulfate is in coexistence with the reaction system of fatty acid ester and $SO_3$, there is less tendency for ester linkage to be broken during the manufacturing process with the attendant lowered coloration (or color tone).

According to one aspect of this invention, there is provided a method for manufacturing α-sulfo fatty acid ester salt which comprises the steps of sulfonating a mixture of 100 parts by weight of saturated fatty acid alkyl ester having 9 to 26 carbon atoms and less than 10 parts by weight of inorganic sulfate by sulfonating gas containing 1.0 to 2.0 mols of $SO_3$ per mol of said fatty acid ester and diluted to a concentration of 3 to 20 % by volume by inert gas at a higher reaction temperature than the solidification point of said fatty acid ester, followed by neutralization by caustic alkali.

DETAILED DESCRIPTION OF THE INVENTION

Saturated fatty acid alkyl ester as used in this invention has a fatty acid residual radical having 8 to 22 carbon atoms and an alcohol residual radical having 1 to 6 carbon atoms, both residual radicals having 9 to 26 carbon atoms in all. As fatty acid, use is made of, for example, capric acid, lauric acid, myristic acid, palmitic acid, stearic acid, hydrogenated coconut fatty acid, hydrogenated palm oil fatty acid, hydrogenated tallow fatty acid and synthetic fatty acid. Said synthetic fatty acid is straight-chain or branched fatty acid synthesized from α-olefin and carbon monoxide. As alcohol, use is made of methanol, ethanol, propanol, butanol etc. Fatty acid ester may be used singly or in combination, but the iodine value is preferred to be less than 1.

Inorganic sulfate as used in this invention is not particularly limited so far as it is anhydrous powder. For instance, use may be made of sodium sulfate, calcium sulfate, aluminum sulfate, ferric sulfate, ammonium sulfate etc., but sodium sulfate is most preferred. The amout of said inorganic sulfate used is chosen to be less than 10 parts by weight or preferably 0.5 to other smaller volumes than 10 parts by weight based on 100 parts by weight of the fatty acid ester. If said amount is increased to 10 parts by weight or over, the reaction liquid will be unduly viscous, failing to attain a full gas-liquid contact. Application of more than 0.5 part by weight of the inorganic sulfate can attain the object of this invention, though said amount somewhat varies with the particle size of said inorganic sulfate.

A sulfonating gas is diluted to a concentration of 3 to 20% by volume by inert gas such as nitrogen and air, and contains 1.0 to 2.0 mols, preferably 1.2 to 1.8 mols, of $SO_3$ per mol of raw-material fatty acid ester. For $SO_3$ less than this amount, no sufficient sulfonation proceeds. For $SO_3$ greater than this amount, on the other hand, the sulfonation reaction is more drastically effected, resulting in pronounced coloration due to local overheating. The $SO_3$ gas can be obtained by evaporating liquid $SO_3$ or burning sulfur.

The reaction temperature is at least required to be high enough to permit fatty acid ester to be liquidified, but the temperature per se constitutes no important requirement. In general, however, the reaction temperature is selected to be in a range of the solidification point of the fatty acid ester to a point 100° C higher than the solidification point, preferably the solidification point to the point 50° C higher than the solidification point. The reaction time somewhat varies whether a batch type of a continuation type is adopted, but it is in a range of about 10 to 120 minutes.

Where the sulfonation reaction product is digested, it is suitable to maintain it 10 to 120 minutes at 60° to 90° C. It is preferred that neutralization be carried out in an acidic or weakly alkaline state. As alkali, use is made of about 1 to 20 weight percent of an aqueous solution of alkali such as caustic soda, caustic potassium etc. bleaching treatment can be conducted before or after neutralization. To α-sulfo fatty acid ester manufactured according to this invention is added inorganic or organic builder or the other additives to obtain a detergent composition.

This invention will now be explained by way of example as follows:

EXAMPLE 1

333g (1.15 moles) of hydrogenated tallow fatty acid methyl ester and 3.3g of powdered sodium sulfate (first class grade reagent powdered sodium sulfate of 40 to 60 mesh) were charged into a jacket-cooled, 1l glass reactor equipped with a stirrer and, when a temperature reached 80° C, 120g (1.5 moles) of $SO_3$ gas diluted by a $N_2$ gas to 5 volume percent was introduced 40 minutes into the reactor with uniform velocity. After stirring continues 10 minutes at the same temperature, the obtained sulfonated product was neutralized at 50° C with 4% caustic soda aqueous solution to yield a slurry-like product. The result is shown in Table below.

It is to be noted that the results of the following Control and Examples are also shown in Table.

Control

The process of Example 1 was repeated without using sodium sulfate, providing a slurry-like product.

EXAMPLE 2

333g (1.15 moles) of hydrogenated tallow fatty acid methyl ester, together with 16.7g of powdered sodium sulfate (first class grade reagent powdered sodium sulfate manufactured by Junsei Kagaku Co., Ltd.) was charged into a jacket-cooled, 1l glass reactor equipped with a stirrer and, after a temperature reached 80° C, 120g (1.5 moles) of $SO_3$ gas diluted by a $N_2$ gas to 5 volume percent was introduced 40 minutes into the reactor with uniform velocity. After stirring continued 10 minutes at the same temperature, the obtained sulfonated product was neutralized at 50° C with a 4% caustic soda aqueous solution to yield a slurry-like product.

EXAMPLE 3

333g (1.15 moles) of hydrogenated tallow fatty acid methyl ester and 33.3g of powdered sodium sulfate (a first class grade sodium sulfate manufactured by Junsei Kagaku Co., Ltd.) were charged into a jacket-cooled, 1l glass reactor equipped with a stirrer and when a temperature reach 80° C, 120g (1.5 moles) of $SO_3$ gas diluted by a $N_2$ gas to 5 volume percent was admitted 40 minutes into the reactor with uniform velocity. After stirring continued 10 minutes at the same temperature, the obtained sulfonated product was neutralized at 50° C with a 4% caustic soda aqueous solution to yield a slurry-like product.

EXAMPLE 4

333g (1.15 moles) of hydrogenated tallow fatty acid methyl ester and 16.7g of powdered calcium sulfate (a first class grade reagent powdered calcium sulfate manufactured by Junsei Kagaku Co., Ltd.) were charged a jacket-cooled, 1l glass reactor provided with a stirrer and when a temperature reached 80° c, 120g (1.5 moles) of $SO_3$ gas diluted by a $N_2$ gas to 5 volume percent was admitted 40 minutes into the reactor with uniform velocity. After stirring continued 10 minutes at the same temperature, the obtained sulfonated product was neutralized at 50° C with a 4% caustic soda aqueous solution to yield a slurry-like product.

EXAMPLE 5

333g (1.15 moles) of hydrogenated tallow fatty acid methyl ester and 16.7g of powdered ferric sulfate (a first class grade reagent powdered ferric sulfate manufactured by Junsei Kagaku Co., Ltd.) were charged into a jacket-cooled, 1l glass reactor with a stirrer and, when a temperature reached 80° C, 120g (1.5 moles) of $SO_3$ gas diluted by a $N_2$ gas to 5 volume percent was introduced 40 minutes into the reactor with uniform velocity. After stirring continued 10 minutes at the same temperature, the obtained sulfonated product was neutralized at 50° C with a 4% caustic soda aqueous solution to yield a slurry-like product.

EXAMPLE 6

333g (1.15 moles) of hydrogenated tallow fatty acid methyl ester and 16.7g of powdered aluminum sulfate (a first class grade aluminum sulfate manufactured by Junsei Kagaku Co., Ltd.) were charged into a jacket-cooled, 1l glass reactor equipped with a stirrer and, when a temperature reached 80° C, 120g (1.5 moles) of $SO_3$ gas diluted by a $N_2$ gas to 5 volume percent was admitted 40 minutes into the reactor with uniform velocity. After stirring continued 10 minutes at the same temperature, the obtained sulfonated product was neutralized at 50° C with a 4% caustic soda aqueous solution to yield a slurry-like product.

Table

|  | Example 1 | Control | Examples 2 | 3 | 4 | 5 | 6 |
| --- | --- | --- | --- | --- | --- | --- | --- |
| Amount of sulfate added (g) | Sodium sulfate 3.3g |  | Sodium sulfate 16.7g | Sodium sulfate 33.3g | Calcium sulfate 16.7g | Ferric sulfate 16.7g | Aluminum sulfate 16.7g |
| Sulfonation percentage (%) | 96.5 | 98.0 | 98.6 | 98.0 | 97.6 | 97.4 | 96.9 |
| α-sulfo fatty acid ester monoalkali salt percentage (%)* | 86.1 | 81.5 | 95.2 | 89.8 | 87.7 | 88.3 | 86.5 |
| Color** | 950 | 2000 | 500 | 600 | 1200 | 1100 | 1200 |
| Percentage of alcohol-insoluble matter (%)*** | 2.1 | 1.3 | 5.1 | 8.3 | 4.7 | 4.9 | 5.3 |

*α-sulfo fatty acid ester monoalkali salt percentage

Table -continued

| | Example 1 Control | 2 | 3 | Examples 4 | 5 | 6 |
|---|---|---|---|---|---|---|

$$= \frac{\alpha\text{-sulfo fatty acid ester monoalkali salt}}{\alpha\text{-sulfo fatty acid ester monoalkali salt} + \alpha\text{-sulfo fatty acid dialkali salt}} \times 100$$

**color tone measurement requirement:
Sample = a 3% aqueous solution of active ingredient
absorbancy method = (using a 139 type spectrophotometer manufactured by Hitachi, Ltd.) Wavelength 420 mμ   Slit width 0.05 mm
Numeral representation = measured absorbancy  (−log T) × 10³
***alcohol-insoluble matter:
remainder obtained by eliminating α-sulfo fatty acid dialkali salt from all alcohol-insoluble matter (the percentage shows a value against a total amount of α-sulfo fatty acid ester mono alkali alkali salt and α-sulfo fatty acid dialkali salt)

What we claim is:

1. A method for the manufacture of α-sulfo fatty acid ester salt which comprises:

sulfonating a mixture of 3 parts by weight of saturated fatty acid alkyl ester having 9 to 26 carbon atoms and 0.5 to 10 parts by weight of inorganic sulfate selected from the group consisting of sodium, calcium, ferric, aluminum and ammonium sulfates with a sulfonating gas containing about 1 to 2 mols of $SO_3$ per mol of said fatty acid ester diluted to a concentration of between about 3 to 20% by volume with an inert gas, said sulfonation being conducted at a temperature higher than the solidification point of said fatty acid ester, and thereafter neutralizing the resulting α-sulfo fatty acid ester with caustic alkali.

2. The method of claim 1 wherein said inorganic sulfate is an anhydrous powder.

3. The method of claim 1 wherein said ester is the esterification product of a saturated fatty acid having 8 to 22 carbon atoms and an alcohol having 1 to 6 carbon atoms.

4. The method of claim 1 wherein said ester has an iodine value less than 1.

5. The method of claim 3 wherein said fatty acid is selected from the group consisting of capric, lauric, myristic, plamitic, stearic, hydrogenated tallow fatty, hydrogenated coconut oil fatty, and hydrogenated palm oil fatty acids.

6. The method of claim 3 wherein said fatty acid is synthetic fatty acid synthesized form α-olefin and carbon monoxide.

7. The method of claim 3 wherein said alcohol is selected from the group consisting of methanol, ethanol, propanol and butanol.

* * * * *